(12) United States Patent
Takamoto et al.

(10) Patent No.: US 7,063,710 B2
(45) Date of Patent: Jun. 20, 2006

(54) INTRACARDIAC SUTURE DEVICE

(75) Inventors: Shinichi Takamoto, Tokyo-to (JP);
Yoshihiro Suematsu, Tokyo-to (JP);
Katsuya Miyagawa, Osaka (JP);
Hideaki Kataoka, Osaka (JP)

(73) Assignee: Nipro Corporation, Osaka (JP)

( * ) Notice: Subject to any disclaimer, the term of this patent is extended or adjusted under 35 U.S.C. 154(b) by 545 days.

(21) Appl. No.: 10/413,524

(22) Filed: Apr. 15, 2003

(65) Prior Publication Data

US 2003/0195529 A1    Oct. 16, 2003

(30) Foreign Application Priority Data

Apr. 15, 2002   (JP) .............................. 2002-112183

(51) Int. Cl.
*A61B 17/04*  (2006.01)

(52) U.S. Cl. ...................................... 606/144; 606/139
(58) Field of Classification Search ................ 606/139, 606/144, 145, 148; 600/104
See application file for complete search history.

(56) References Cited

U.S. PATENT DOCUMENTS

| | | | | |
|---|---|---|---|---|
| 4,841,888 A | * | 6/1989 | Mills et al. ................. | 606/145 |
| 5,037,433 A | * | 8/1991 | Wilk et al. .................. | 606/139 |
| 5,080,663 A | | 1/1992 | Mills et al. | |
| 5,716,367 A | * | 2/1998 | Koike et al. ................ | 606/144 |
| 5,792,153 A | | 8/1998 | Swain et al. | |
| 6,280,460 B1 | | 8/2001 | Bolduc et al. | |
| 6,368,334 B1 | * | 4/2002 | Sauer ......................... | 606/139 |

FOREIGN PATENT DOCUMENTS

EP        1 297 787 A       4/2003

* cited by examiner

*Primary Examiner*—Julian W. Woo
(74) *Attorney, Agent, or Firm*—Birch, Stewart, Kolasch & Birch, LLP (57) ABSTRACT

An intracardiac suture device comprises a first shaft assembly 1 including a first shaft 11 and a first suture needle-holding device 4 provided at a distal end of the first shaft 11; a second shaft assembly 2 comprising a second shaft 21; a third shaft assembly 3 comprising a third shaft 31 and a handling portion 33; and a puncture assembly 5 provided at a proximal end thereof with a second suture needle-holding device 51. The second shaft 21 is protrusible by sliding-movement from the distal end of the first shaft 11 toward the first suture needle-holding device 4, and a suture needle 6 is transferable between the first suture needle-holding device 4 and the second suture needle-holding device 51 when the third shaft 31 is slid to the distal end of the second shaft 21 after sliding the second shaft 21 to a position where a suture site is held between the second shaft 21 and the first suture needle-holding device 4.

6 Claims, 12 Drawing Sheets

INTRACARDIAC SUTURE DEVICE

BACKGROUND OF THE INVENTION

The present invention relates to an intracardiac suture device for use in treatment of intracardiac defects by suturing the defective portion with a suture needle.

For treatment of intracardiac defects such as atrial septal defect, ventricular septal defect and valvular disease, it is general practice to perform surgical operations with an artificial heart-lung machine (i.e., an extracorporeal circulation system). The heart-lung machine is a device, which performs hemoperfusion instead of the heart of a patient during the stopped period of the pumping action of the heart and acts the breathing function for the lung by prosecution of the gas exchange in the blood. The heart-lung machine generally comprises four main components, i.e., a blood pump, an oxygenator, a heat exchanger and a reservoir. The heart-lung machines have been used widely as auxiliary measures for extracorporeal circulation in open-heart surgery. Further, they have also been used as auxiliary measures for supplementary circulation when any bad circulation of the internal organ and/or organization arises from considerable decrease in the pumping action of the heart, or auxiliary measures for gas exchange when the function of the patient's lung is considerably damaged. In addition, the lung-heart machines are used in membrane oxygenator-assisted extracorporeal circulation (ECMO), and as auxiliary measures for extracorporeal circulation in thoracic aortic aneurysm surgery.

In the first era of cardiac surgery, surgical operations of pulsating hearts have been carried out blindly by the feel and thus the safety has come up as a serious problem before development of an artificial heart-lung machine. In 1953, Dr. Gibbon succeeded in a first cardiac surgery with an artificial heart-lung machine. From that time, the safety of the cardiac surgery has been improved by various improvements in heart-lung machines and development of myocardial depressants. Now, the use of extracorporeal circulation makes it possible to perform the cardiac surgery safely.

However, even at the present state of the art, the cardiac surgeries with the heart-lung machines are at risk for the following postoperative complications:

(1) Complication in the brain: Cerebral hypoxemia or cerebral edema resulting from incorrect perfusion. Cerebral infarction due to embolization by of tissue fragments into the blood caused by interfusion of intake-air into extracorporeal circulation in the heart-lung machine or by operation to connect the heart-lung machine to the patient;

(2) Complication in the lung: hypoxemia or ventilatory insufficiency caused by various inflammatory substances, which are activated by the heart-lung machine;

(3) Renal dysfunction: Acute renal failure caused by decrease in renal blood flow due to use of the heart-lung machine;

(4) Blood cell injuries: Blood cell injuries are taken place by performing perfusion of the blood into the artificial, i.e., heart-lung machine. This may cause renal dysfunction, resulting in necessity of blood infusion;

(5) Postoperative bleeding: Postoperative bleeding may occur by the disorder of the in-vivo hemostatic function caused by the heart-lung machine;

(6) Aortic dissection: By insertion of an arterial inflow cannula into the aorta, the endothelium of the blood vessel may be injured and induced the acute aortic dissection. This complication is extremely serious condition and death rate of a patient is high;

(7) Other complications: Postoperative infective diseases and multiple organ failure caused by decrease of immunoreaction.

It is often the case that these complications cause systemic inflammation even if the patient's condition is not severe and the length of postoperative stay in the hospital takes one week at the least. Further, the artificial circulation passage used in operation is of disposable, a high medical cost presents problems for the patients.

Recently, a tendency to avoid the side effects due to use of the artificial hear-lung is seen in the field of coronary artery bypass, and operations without use of the artificial hear-lung machine have been popularized. In particularly, minimally invasive surgery employing an endoscope is widely used and has become of major interest lately because of low occurrence of complications and rapid recovery after operation.

Even in the field of cardiac surgery, there is an increasing demand for intracardiac surgeries which can be performed without use of any hear-lung machine. It is however, impossible to stop the beat of the heart. Further, it is pointed out that there would be considerable difficulty in use of the endoscope since the blood and beating heart obstructs the view from the endoscope. Commercially available catheter devices such as "Amplatzer" (brand name), "Angelwing" (brand name) are applied for treatment of atrial septal defects. These devices are designed for uniformly distributed defects as targets. Thus, it is difficult with such devices to treat the intracardiac defects since these defects vary with the individual patient. For these reasons, there is a great demand for any breakthrough for realizing cardiac surgery without use of any artificial heart-lung machine.

SUMMARY OF THE INVENTION

It is therefore an object of the present invention to provide an intracardiac suture device for performing minimally invasive cardiac surgery on intracardiac defects without use of any artificial heart-lung system.

The present invention has been made on the basis of an idea that the minimally invasive surgery can be achieved by a method of introducing a suture device into the heart of a patient through a sheath after surgically incising the chest region of a patent.

According to the present invention, there is provided an intracardiac suture device, comprising: a first shaft assembly comprising a first shaft having a lumen passing therethrough from a proximal end to a distal end thereof, a first suture needle-holding means coaxially provided at and spaced from the distal end of the first shaft, and a connector with a hemostatic valve provided on the proximal end of the first shaft;

a second shaft assembly comprising a second shaft slidably arranged in the first shaft assembly, and a connector with a hemostatic valve provided on the proximal end of the second shaft, said second shaft having first and second lumens passing therethrough from a proximal end thereof to a distal end thereof, said second lumen being closed at a distal end thereof with a transparent covering member;

a third shaft assembly comprising a hollow third shaft slidably arranged in the first lumen of said second shaft assembly, and a handling portion provided at a proximal end of the third shaft; and a puncture assembly comprising a hollow operating rod provided at a distal end thereof with a second suture needle-holding means movably arranged in the distal end of the third shaft, said hollow operating rod being connected to the proximal end of the second suture needle-holding means and movably arranged in the third shaft assembly;

and a visual monitoring means arranged in the distal end of the second lumen at a position close to the distal end of said cover member;

wherein said second shaft is protrusible by sliding-movement from the distal end of the first shaft toward the first suture needle-holding means, and wherein a suture needle is transferable between the first suture needle-holding means and the second suture needle-holding means when the third shaft is slid to the distal end of the second shaft after sliding the second shaft to a position where a suture site is held between said covering member and the first suture needle-holding means.

Preferably, the second shaft assembly is rotatable in the first shaft assembly. The above visual monitoring means may be an endoscope or ultrasonic transducer. Further, the second connector may be provided with a pair of rotationally symmetrical protrusion extending from the peripheral portion toward the distal end thereof, and the first connector may be provided on its proximal end side with a pair of recesses for holding the protrusions of the second connector. In this case, the second shaft is movable between a position where the protrusions are respectively fitted in the recesses and a position where the protrusions are disengaged from the recesses. Either or both connectors of the first and second shaft assemblies may be provided with a side tube for infusion of heparin, a saline solution or the like.

The present invention will be explained below, making reference to the accompanying drawings, which show, by way of example only embodiments thereof.

DETAILED DESCRIPTION OF THE INVENTION

Referring now to FIGS. 1 to 5, there is shown an intracardiac suture device according to the present invention, which comprises: a first shaft assembly 1 comprising a first shaft 11 and a first suture needle-holding means (or a first suture needle gripper) 4; a second shaft assembly 2 comprising a second shaft 21 having first and second lumens 211, 212 and a distal end closed by a transparent covering member 23; a third shaft assembly 3 comprising a hollow third shaft 31 and a handling portion 33; and a puncture assembly 5 provided with a second suture needle-holding means 51. The second suture needle-holding means 51 being removably arranged in the distal end of the third shaft 31; and an endoscope 8; wherein a suture needle 6 is adapted to be transferable between the first suture needle-holding means 4 and the second suture needle-holding means 51 when the third shaft 31 is slid to the distal end of the covering member 23 after sliding of the second shaft 21 to a position where a suture site is clamped between the covering member 23 and the first suture needle-holding means 4.

Figure 4:
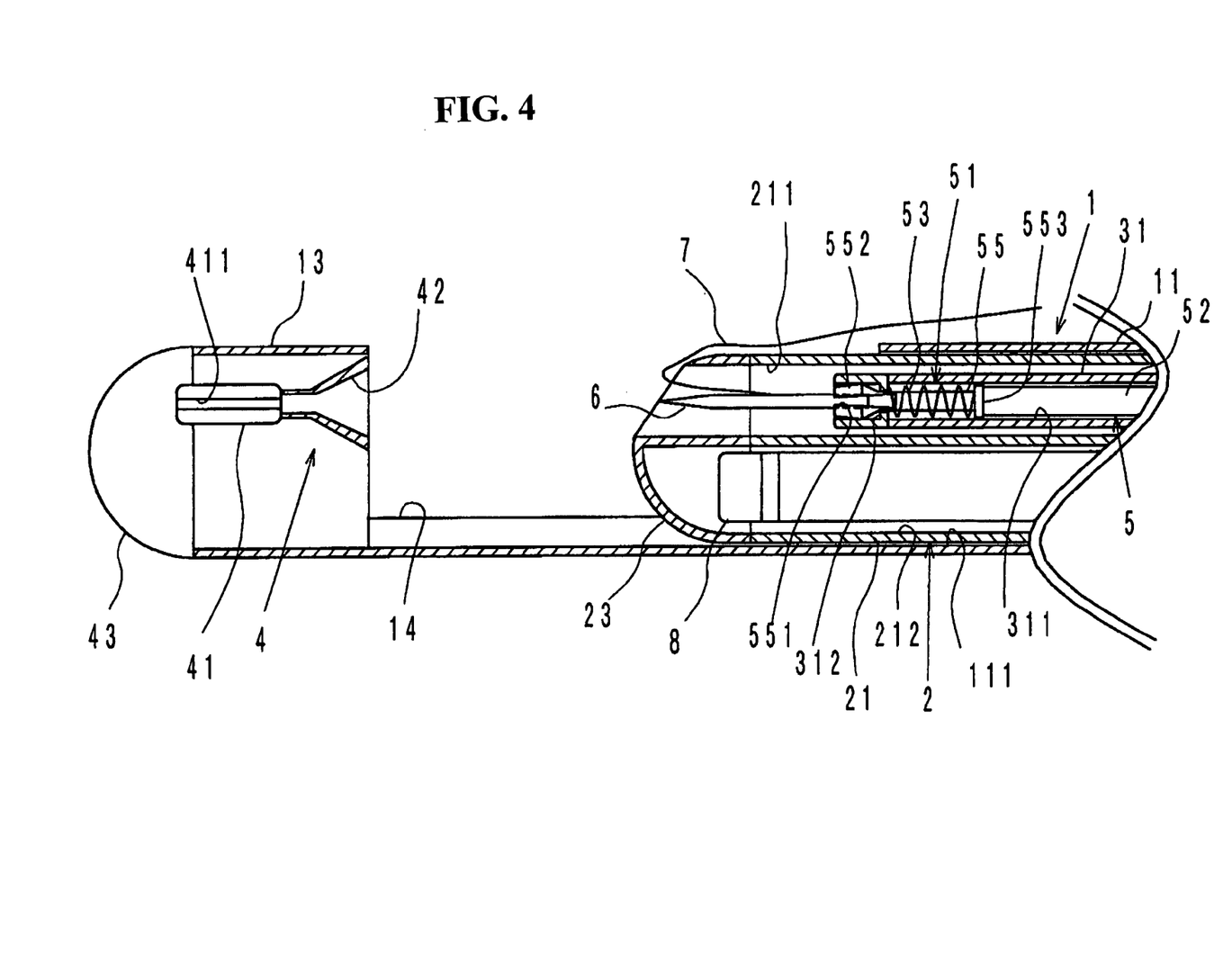
FIG. 4 is an enlarged sectional view of a distal portion of the suture device of FIG. 1, including the first and second suture-holding portion thereof.
Figure 5:
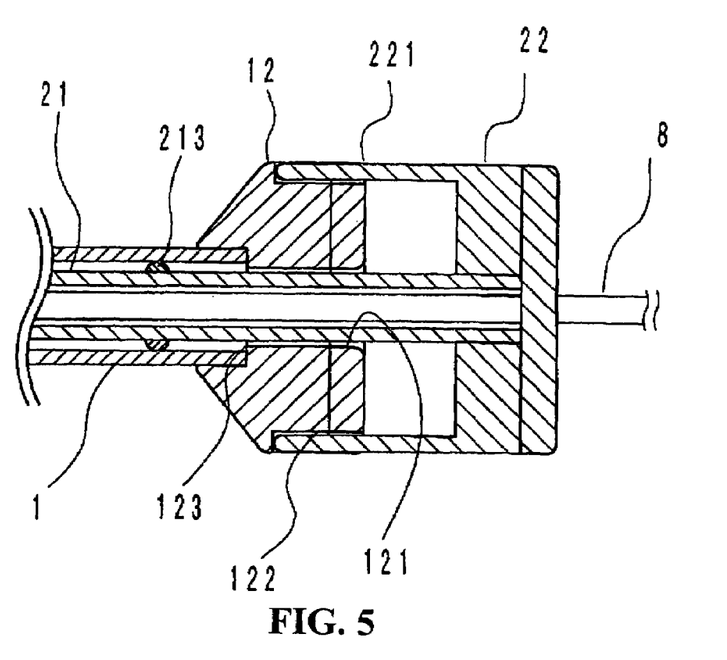
FIG. 5 is an enlarged sectional view partially taken along a line A–A' in FIG. 1.

As illustrated in FIG. 4, the first shaft assembly 1 comprises a first shaft 11 with a lumen 111 extending from a proximal end thereof to a distal end thereof and passing therethrough, a first suture needle-holding means 4 coaxially provided at a distal end of the first shaft 11 and spaced therefrom, and a first connector 12 provided on the proximal end of the first shaft 11 and having a hemostatic valve.

The first shaft 11 is a tubular member made of a metal such as stainless steel and brass, meshed or coiled stainless steel, or a synthetic resin such as fluoroplastic (e.g., polytetrafluoroethylene), polypropylene, polyethylene, polyamide, polyethylene terephthalate, polyurethane and the like. Th first shaft 11 has lumen 111, which passes therethrough from the distal end thereof to the proximal end thereof. The second shaft assembly 2 is slidably and rotatably attached to the first shaft assembly 1 by inserting the second shaft 21 into the lumen 111 of the first shaft 11 through the connector 12 provided on the proximal end of the first shaft 11.

The first connector 12 is a tubular member generally made of a synthetic resin such as polypropylene, ABS (acrylonitrile-butadiene-styrene) resin, polyvinyl chloride, polyethylene and polyethylene terephthalate, or a metal such as stainless steel, brass and the like. The first connector 12 is provided at a proximal end thereof with a through-hole 121 for insertion of the second shaft 21. The first connector 12 is provided with a stepped lumen of which a proximal portion has an inner diameter smaller than that of a distal portion thereof. When the second shaft assembly 2 is moved toward the proximal end of the device by relative movement, the relative movement of the second shaft assembly 2 toward the proximal end of the device is stopped by engagement of an annular rib 213 of the second shaft 2 mentioned below with a stepped portion 123 of the first connector 12. The first connector 12 is provided in a sidewall thereof with a pair of opposing grooves 122 into which a pair of protrusions 221 of the connector 22 of the second shaft 21 mentioned below. Thus, the relative movement of the second shaft 21 toward the distal end of the second shaft assembly 2 is stopped when the protrusions 221 are snugly fitted in the corresponding grooves 122 of the first connector 12. The first connector 12 is also provided in an interior thereof with a hemostatic means (not illustrated in the drawings) for preventing leakage of the blood during operation.

Figure 1:
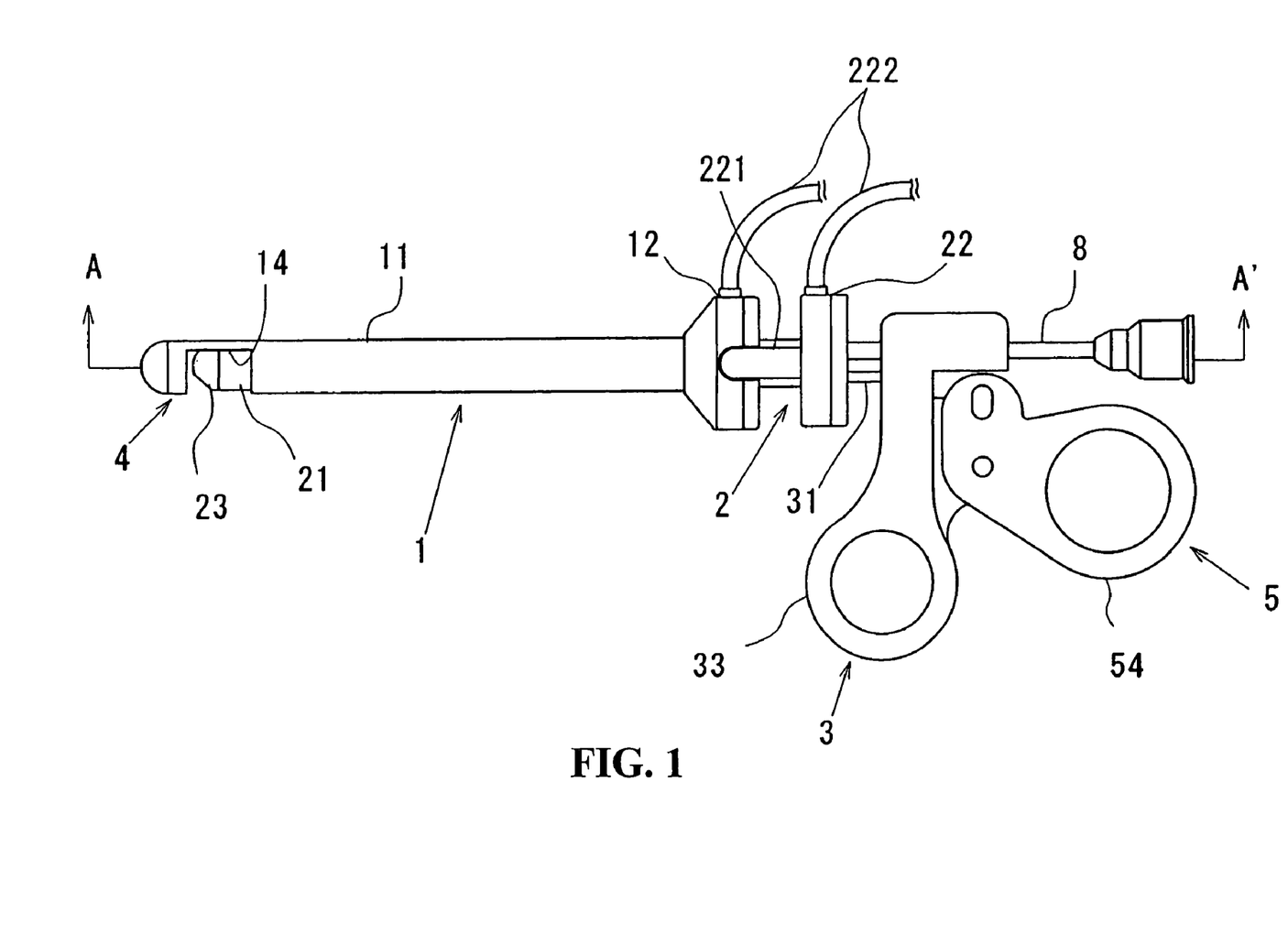
FIG. 1 is a plane view illustrating one embodiment of an intracardiac suture device according to the present invention.

The first suture needle-holding means 4 may be arranged in a needle-holding means housing 13, which is formed as an integral part of a tube forming the first shaft 11. In this embodiment, as illustrated in FIG. 1, the needle-holding means housing 13 is provided at the distal end of the tube, which forms the first shaft 11. The needle-holding means housing 13 is spaced from the distal end of the first shaft 11 by a notch 14 formed in the distal end of the first shaft 11. The notch 14 has a predetermined length and a depth sufficiently greater than a radius of the first shaft 11. The needle-holding means housing 13 is closed at the distal end thereof by a closing member 43 to which the first suture needle-holding means 4, is fixed.

The first suture needle-holding means 4 is arranged in the needle-holding means housing 13 such that the distal end thereof is directed to the first shaft 11. The first suture needle-holding means 4 may be comprised of, as illustrated in FIG. 4, a flexible hollow member 41 including a needle-holding portion with an inner diameter slightly smaller than a diameter of the suture needle 6. The hollow member 41 is provided at a distal end thereof with a needle guide port 42, and at a proximal side thereof with plural slits 411 extending in the longitudinal direction thereof.

The hollow members 41 of the fist suture needle-holding means 4 may be made of a metal such as stainless steel, brass and the like or a flexible resin such as polypropylene, polyethylene, polyamide and the like. The needle guide port 42 may be made of a synthetic resin such as fluoroplastic (e.g., polytetrafluoroethylene), polypropylene, polyethylene, polyamide, polyethylene terephthalate, polyurethane and the like.

As can be seen from FIGS. 1 and 4, the second shaft assembly 2 comprises a second shaft 21 having first and second lumens 211, 212 extending from a distal end thereof to a proximal end thereof and passing therethrough, a transparent cover member 23 attached to the distal end of the second shaft 21 to close the distal end of the second lumen 212, and a connector 22 attached to the proximal end of the second shaft 21 and having a hemostatic valve provided therein. The second shaft 21 is movable by sliding movement in the direction of the first suture needle-holding means 4 and is rotatable within the first shaft assembly 1. The first lumen 211 houses the puncture assembly 5 slidably inserted therein, while the second lumen 212 houses an endoscope arranged therein.

Figure 3:
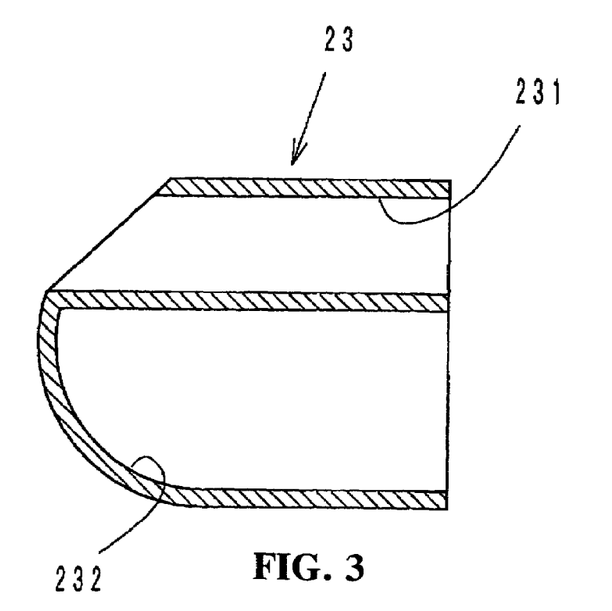
FIG. 3 is an enlarged section view of a covering member shown in FIG. 1.

Any cover member may constitute the cover member 23 if it can protect the endoscope. A non-limitative preferred cover member is the one having a lumen 231 communicated with the first lumen 211 at a proximal end thereof and being open at a distal end thereof, and a lumen 232 communicated with the second lumen 212 at a proximal end thereof and closed at a distal end thereof. The cover member 23 may be made of a transparent plastic such as, for example, acrylic resin, polystyrene, polypropylene, polymethyl methacrylate, polyamide, polyester, polycarbonate and the like.

The second shaft 21 is a slender hollow tubular member made of the same material as that used for the first shaft 11. Into the first and second lumens 211, 212, which pass through the second shaft 21 from the distal end thereof to the proximal end thereof, the third shaft assembly 3 (actually, the third shaft 31 through the connector 22) and endoscope 8 are slidably inserted, respectively.

The second connector 22 is a tubular member made of the same material as that of the connector 12, and is provided at a proximal end thereof with an insertion hole (not illustrated in the drawings) for the third shaft 311 and endoscope 8. The connector 22 is further provided in its interior with a hemostatic means (not illustrated in the drawings) for preventing the blood from leakage during operation.

The third shaft assembly 3 comprises a hollow third shaft 31 and a handling portion 33 provided at a proximal end of the third shaft 31. The third shaft 31 is a slender tubular member made of the same material as that of the first shaft 11 and having a lumen 311 passing therethrough from a distal end thereof to a proximal end thereof. The third shaft 31 is provided at the proximal end thereof with the handling portion 33 for actuating it back and forth by sliding movement, through which an operating rod 52 of an after-mentioned second suture needle-holding means 51 is inserted movably back and forth. There is no limit to a material for the handling portion 33, but the handling portion 33 is generally made of the same as that used for the third shaft 31.

The puncture assembly 5 is slidably arranged in the third shaft assembly 3. The puncture assembly 5 comprises a second suture needle-holding means 51, and a slender hollow operating rod 52 connected to a proximal end of the second suture needle-holding means 51. The second suture needle-holding means 51 is positioned in the distal end of the third shaft 31 and adapted to be put in and out the lumen 311 of the third shaft 31. The operating rod 52 is movably arranged in the lumen 311 of the third shaft 31.

The second suture needle-holding means 51 comprises a flexible hollow member 55 having an inner diameter slightly larger than the diameter of the suture needle 6 and an outer diameter smaller than the inner diameter of the third shaft 31. The hollow member 55 is provided at the distal end thereof with a enlarged head portion 552, which has an outer diameter greater than the inner diameter of the third shaft 31 and is tapered toward the proximal end thereof. The hollow member 55 is provided with plural slits 551 longitudinally extending from the distal end of the head portion 552 towards the proximal end of hollow member 55.

Figure 6:
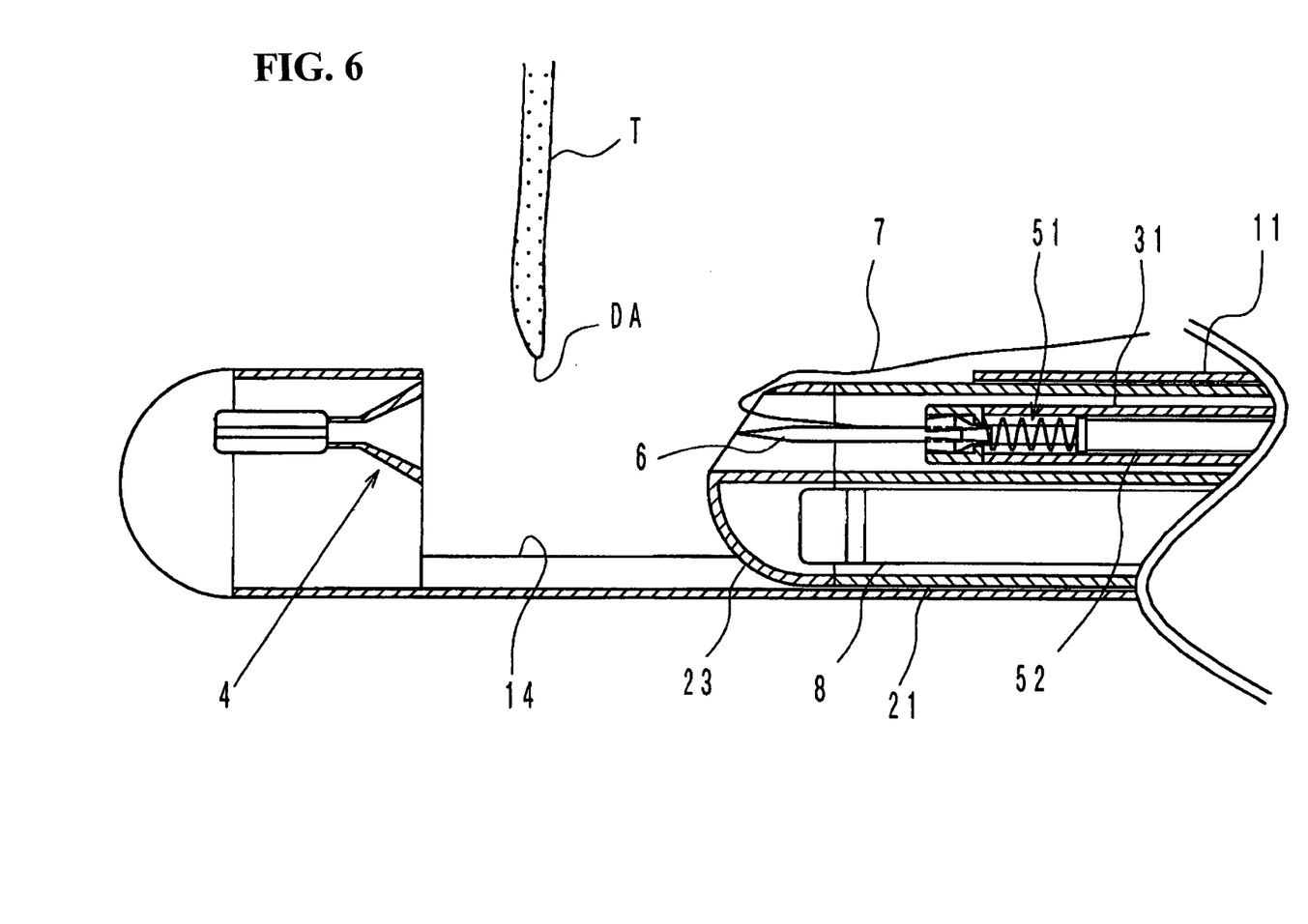
FIG. 6 is a schematic diagram illustrating suture operation using the intracardiac suture device of the present invention.
Figure 7:
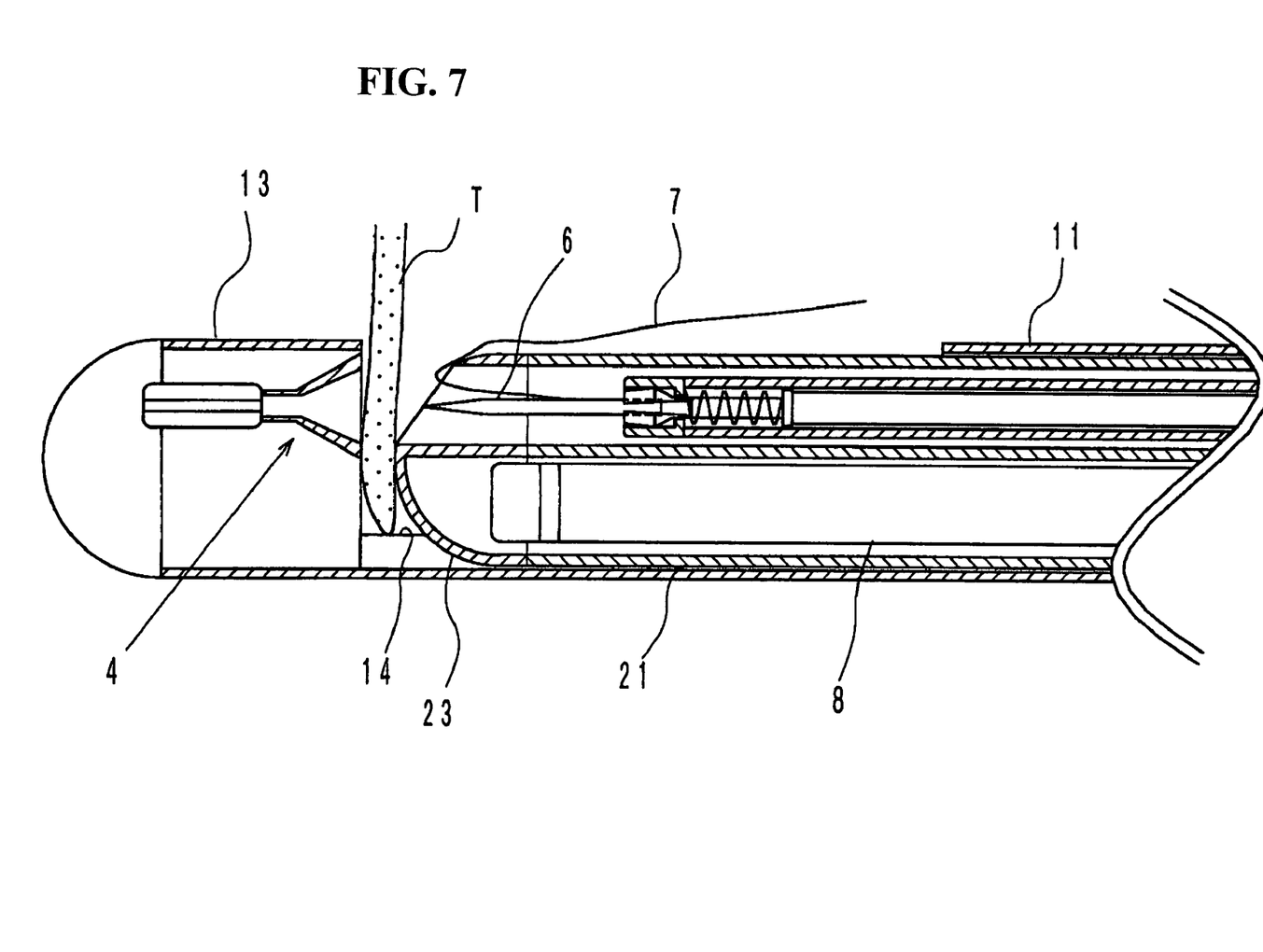
FIG. 7 is a schematic diagram illustrating suture operation using the intracardiac suture device of the present invention.

The hollow operating rod 52 sidably arranged in the lumen 311 of the third shaft 31 is connected to the proximal end of the hollow member 55. The enlarged head portion 552 is adapted to hold the suture needle 6 therein by reduction of the inner diameter thereof when the enlarged head portion 552 is housed in the third shaft 31. In this case, as illustrated in FIGS. 6 and 7, the third shaft 31 is preferably provided with an annular rib 312 at the distal portion of the lumen 311 thereof to prevent the enlarged head portion 552 from movement toward the proximal side thereof at the time of seating of the enlarged head portion 552 in the third shaft 31.

When the enlarged head portion 552 is pushed out of the lumen of the third shaft 31, the enlarged head portion 552 may be returned to the lumen of the third shaft 31 by manually operating the operating rod 52. Alternately, as illustrated in FIG. 4, the enlarged head portion 552 may be returned automatically to its original position by providing an auto-return mechanism, which comprises, for example, a flange 553 provided at the proximal end of the hollow member 55, and a coil spring 53 arranged around the hollow member 55 and between the flange 553 and the annular rib 312 so that the coil spring 53 is compressed when the operating rod 52 is pushed forward in the third shaft 31, and then restored by the restoring force of the coil spring 53 to automatically house the enlarged head portion 552 to the lumen 311 of the third shaft 31.

Further, in order to improve the operationality of the second suture needle-holding means 51, the operating rod 52 may be provided at a proximal end thereof with a handling portion 54, which is adapted to be moved forward and backward with respect to the handling portion 33 of the third shaft assembly 3.

In a suture set comprised of the aforesaid first, second and third shafts assembly 1, 2, 3, puncture member 5 and endoscope 8, the suture needle 6 is transferred between the first suture needle-holding means 4 and the second suture needle-holding means 51 when the third shaft 31 is moved to the distal end of the second shaft 21 that had been moved beyond the distal end of the first shaft 1 to a position where a suture site is held between the second shaft 21 and the first suture needle-holding means 4.

If necessary, the first connector 12 and/or second connector 22 may be provided with a side tube 222 for infusion of heparin, saline for irrigation and the like.

The hollow member 55 of the second suture needle-holding means 51 may be made of, without being limited to, the same materials as those used for the hollow member 41 of the first suture needle-holding means 4 as the hollow member 55 has the same structure and function as those of the hollow member 41 of the first suture needle-holding means 4.

Using the intracardiac suture device of the present invention, closure of defects may be carried out in the manner mentioned below with reference to FIGS. 6 to 13.

Figure 2:
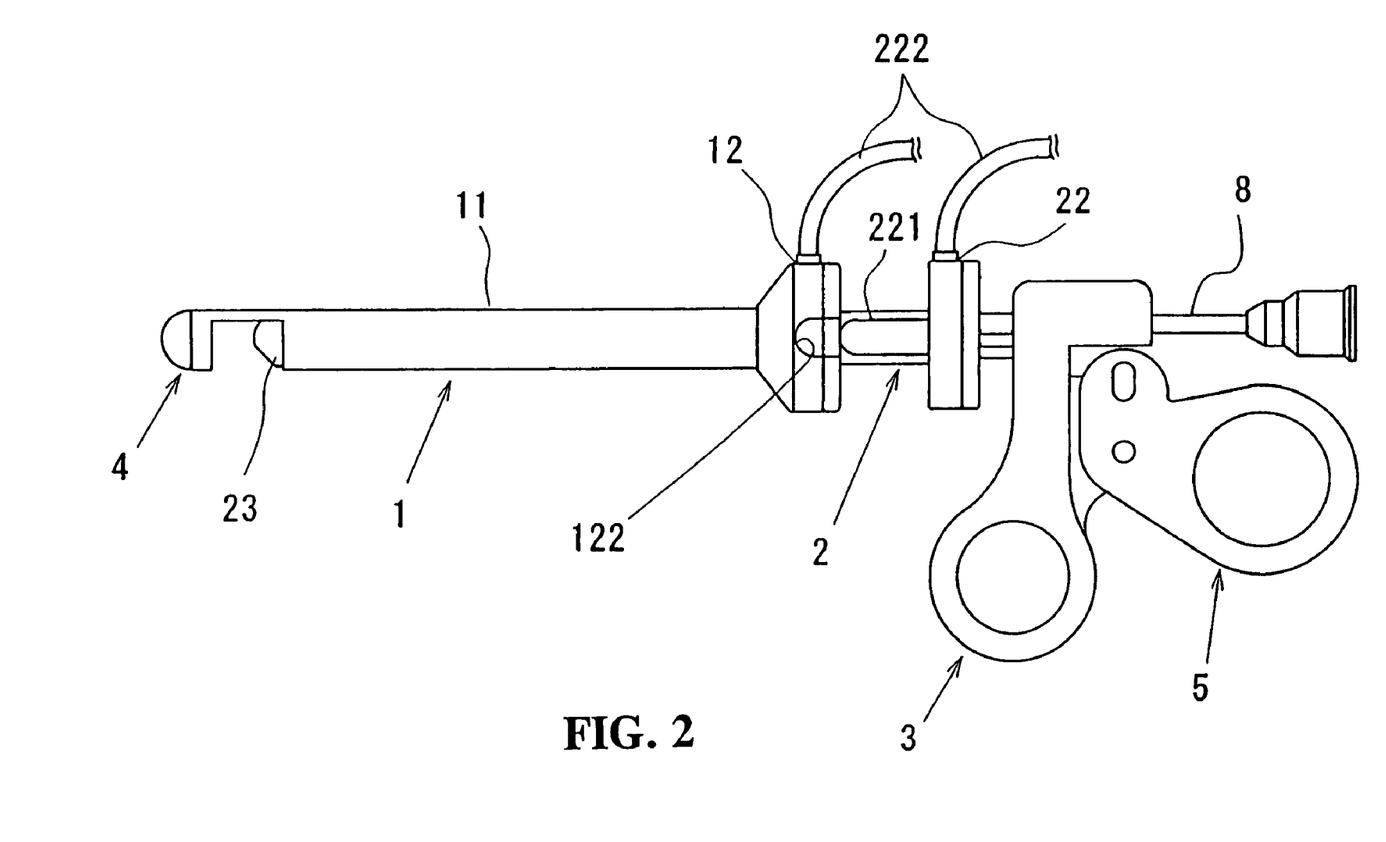
FIG. 2 is a plane view illustrating the intracardiac suture device of FIG. 1, of which the second shaft assembly has been backed away from the first shaft assembly to a certain distance.

Firstly, the heart is exposed by surgical incision of the chest of a patient to check the position of the heart and then punctured at an appropriate part of the heart (usually, the right auricle). A sheath (not illustrated in the drawings) for insertion of an intracardiac suture device is inserted into the heart through the punctured part thereof until a leading end of the sheath reaches to a position near a suture site. Then, the intracardiac suture device illustrated in FIGS. 1 and 2 is inserted into the sheath and guided to the position near the suture site. In that case, the third shaft 31 and the second suture needle-holding means 51 of the suture device have been set so as to have a physical relationship as illustrated in FIG. 4.

Figure 8:
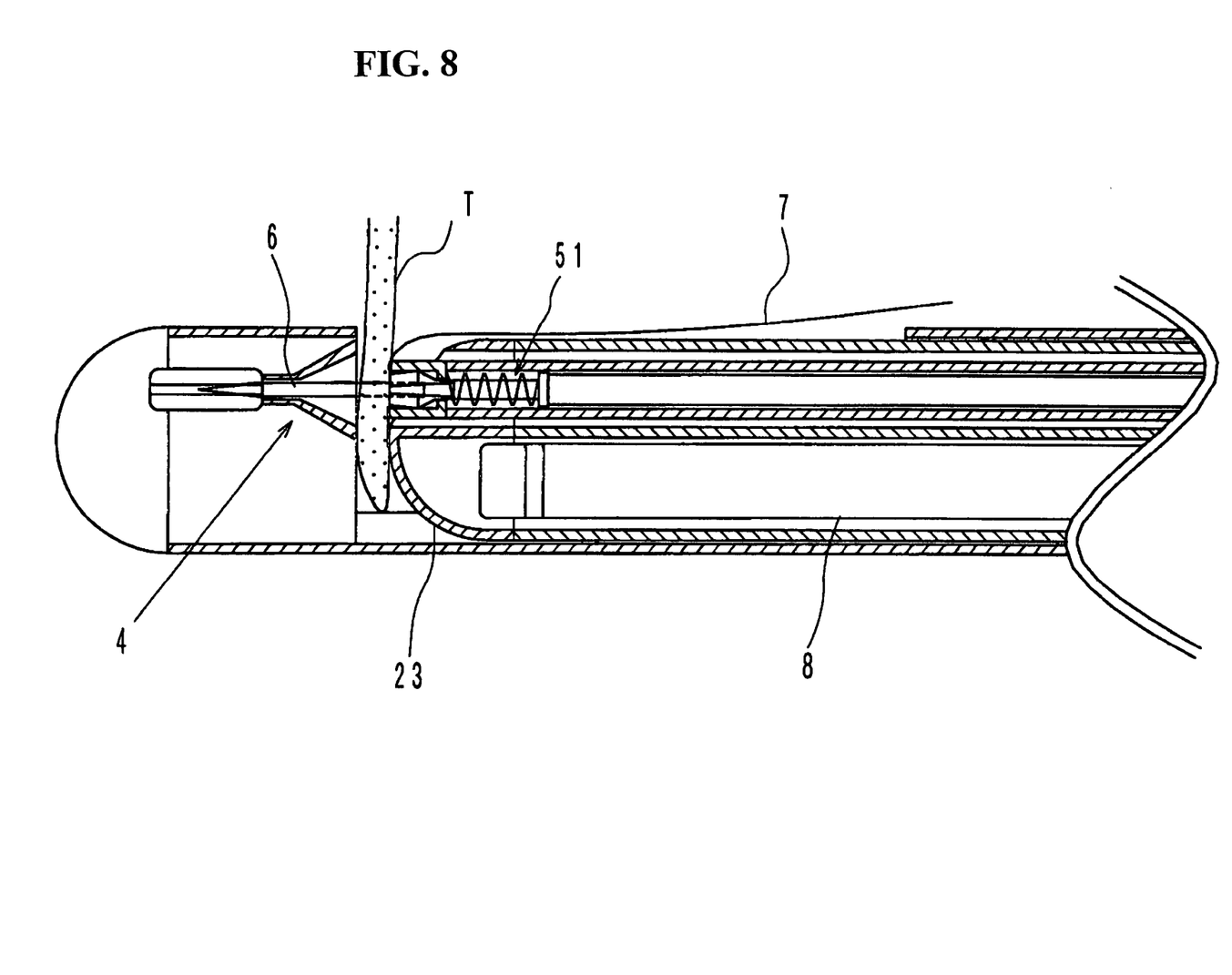
FIG. 8 is a schematic diagram illustrating suture operation using the intracardiac suture device of the present invention.
Figure 9:
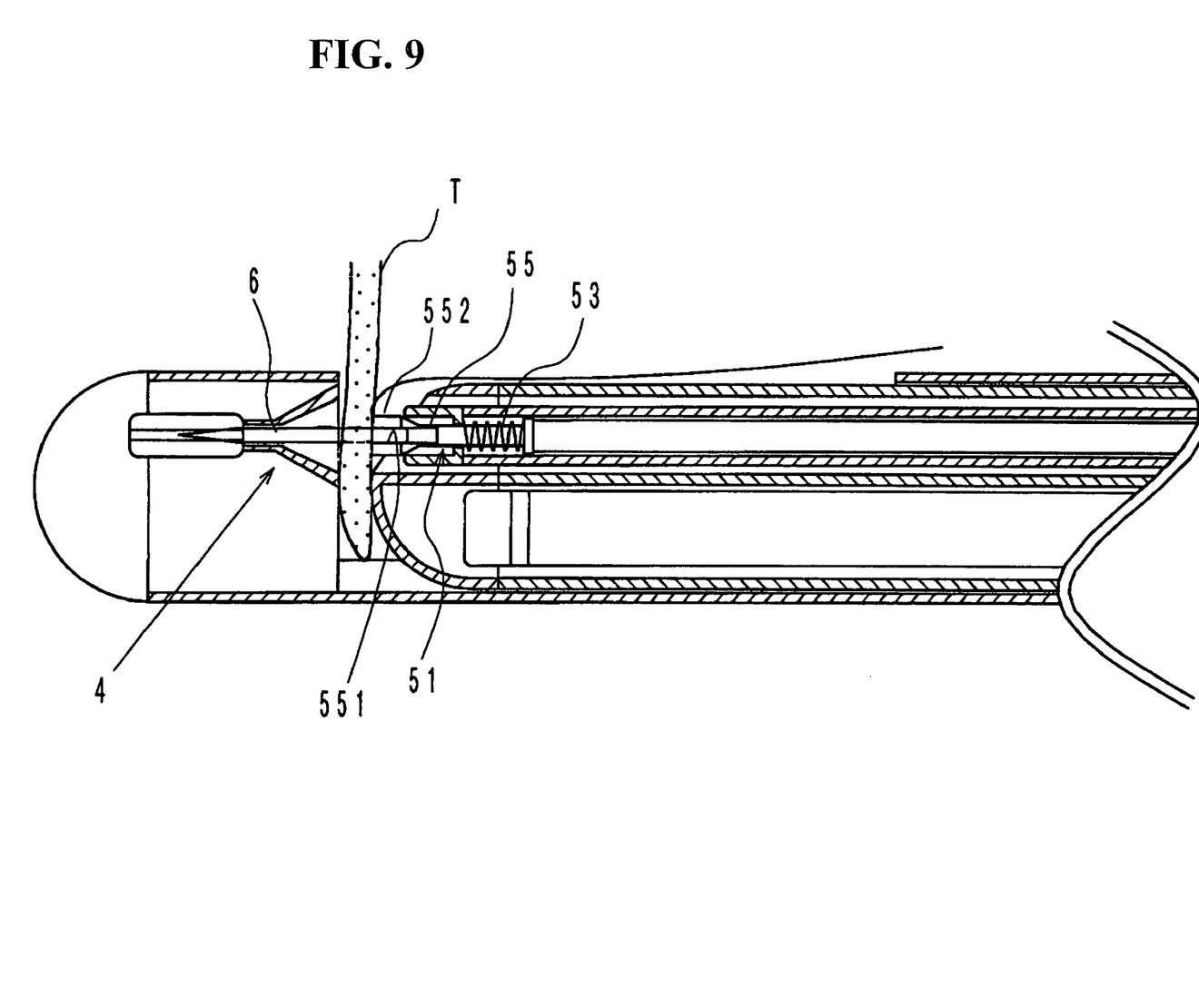
FIG. 9 is a schematic diagram illustrating suture operation using the intracardiac suture device of the present invention.

As illustrated in FIG. 6, the distal end of the suture device is protruded from the sheath to locate the first suture needle-holding means 4 within a defect aperture DA of the heart so that the notch 14 is located in the defect aperture DA. The second shaft assembly 2 is then pushed manually toward the first shaft assembly 1 to hold a tissue T surrounding the defect aperture DA between the distal end of the second shaft 21 and the needle-holding means housing 13, while checking out the physical relationship between the device and the suture site in the heart with the endoscope 8. At that time, the third shaft assembly 3 is moved forward along with the second shaft assembly 2 (FIG. 7). Under the condition of the tissue T that has been held between the needle-holding means housing 13 and the second shaft 21, the third shaft assembly 3 is pushed toward the second shaft assembly 2 by operating the first handling portion 33, with the result that the second puncture needle-holding means 51 housed in the third shaft 31 is moved forward along with the third shaft 31 to puncture the tissue T. Thus, the distal portion of the puncture needle 6 is inserted into the first suture needle-holding means 4 and gripped therein at the distal end thereof (FIG. 8). At that time, it is possible to observe the condition of the suture needle 6 that punctured the tissue T.

Figure 10:
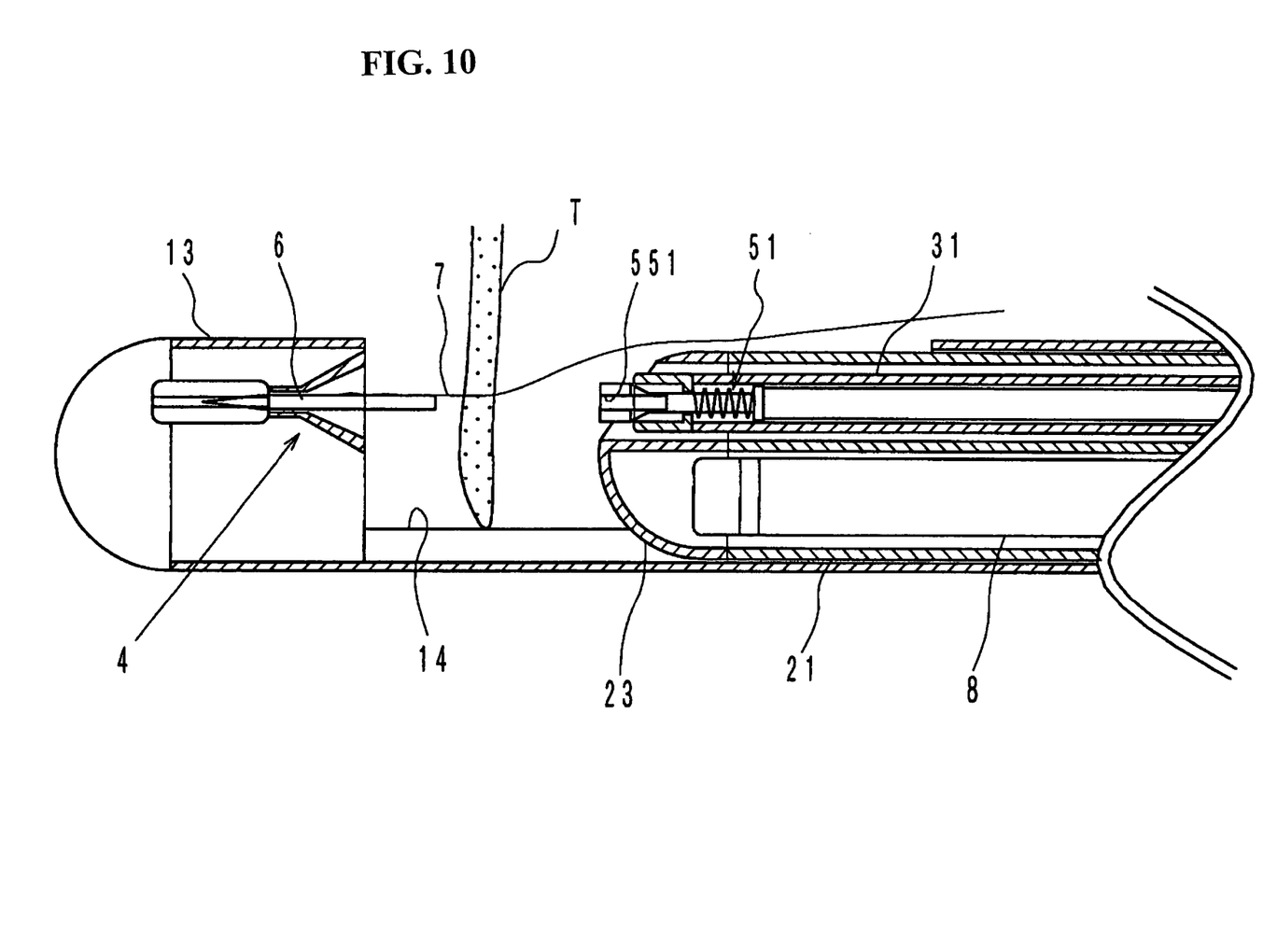
FIG. 10 is a schematic diagram illustrating suture operation using the intracardiac suture device of the present invention.

When the handling portion 33 is moved to a position adjacent to the handling portion 54 (an adjacent condition) by holding the handling portion 33 and 54, the third shaft assembly 3 is backed toward the puncture assembly 5 since the puncture assembly 5 is locked to the first suture needle-holding means 4 by the suture needle 6. At that time, the enlarged head portion 552 is unsheathed from the third shaft 31 and thus the hollow member 55 is released from the compression pressure of the third shaft 31. For this reason, the hollow member 55 is returned to the uncompressed condition where the inner diameter of the hollow member 55 is larger than the outer diameter of the suture needle 6, and the suture needle 6 is released from the second suture needle-holding means 51 (cf. FIG. 9). At the same time, the coil spring 53 is compressed by the backward movement of the handling portion 33. Under that condition, the first shaft assembly 1 is manually pushed forward over the second shaft assembly 2 as it stands, with the result that the suture needle 6 is passed through the tissue T and transferred to the first suture needle-holding means 4 on the opposite side of the second suture needle-holding means 51 with respect to the tissue T, as illustrated in FIG. 10.

Figure 11:
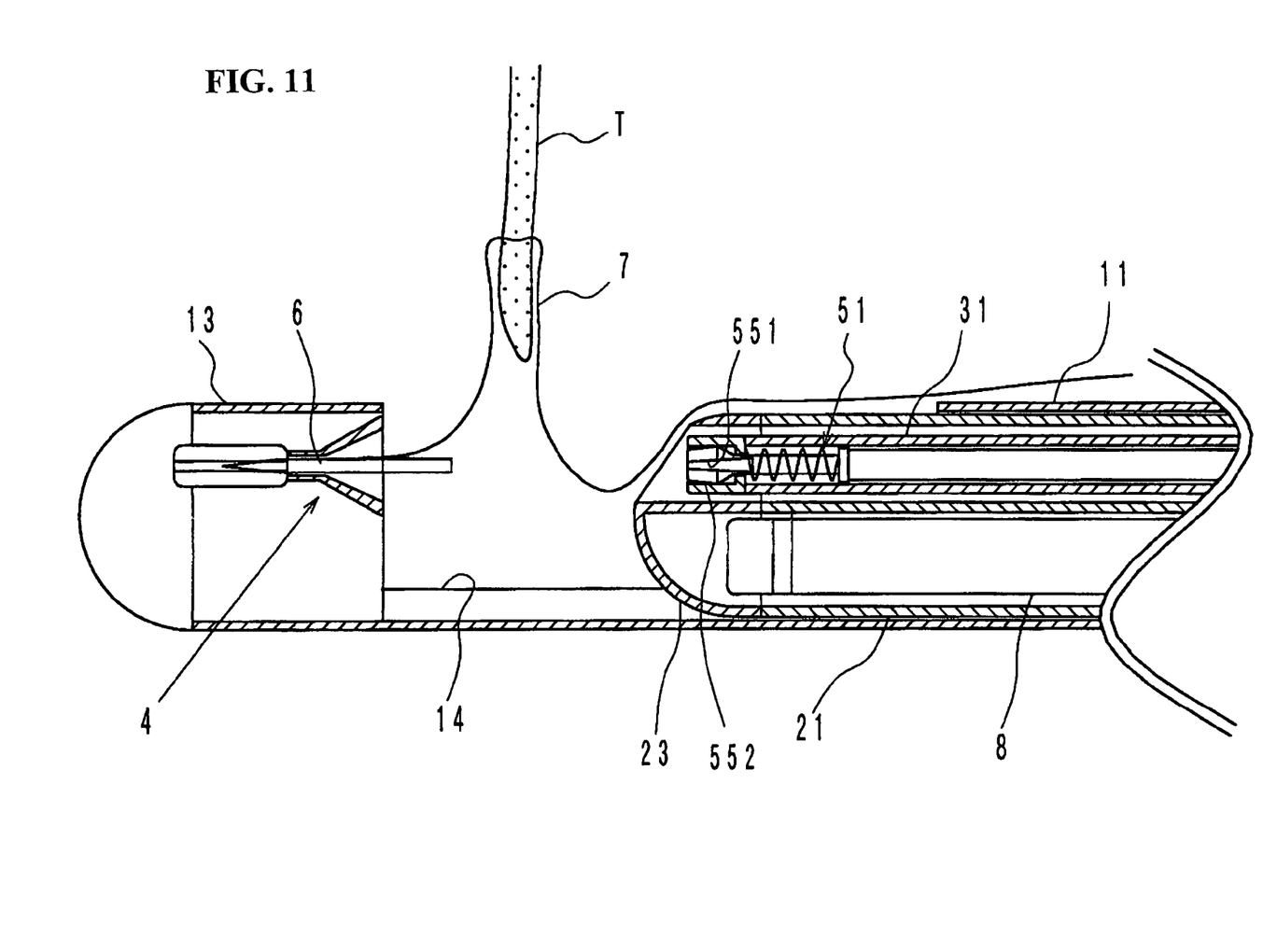
FIG. 11 is a schematic diagram illustrating suture operation using the intracardiac suture device of the present invention.

Then, the whole suture device is somewhat moved backward and the handling portion 54 of the puncture assembly 5 is released from the hand while holding the handling portion 33 by hand, so that the second suture needle holding means 51 is moved backward by the restoring force of the coil spring 53. Thus, the enlarged head portion 552 is pulled in the lumen 311 of the third shaft 31. At that time, the handling portions 33 and 54 are returned from the adjacent condition to the original spaced condition. Under that condition, the whole of the suture device is moved to bring out the tissue T from the notched portion 14, as illustrated in FIG. 11. In this connection, it is possible to observe the conditions of the needle 6 held by the first needle-holding means 4 by rotating the second shaft assembly 2 about the first shaft assembly 1 to coincide the center of the endoscope with the center of the needle guide port 42.

Figure 12:
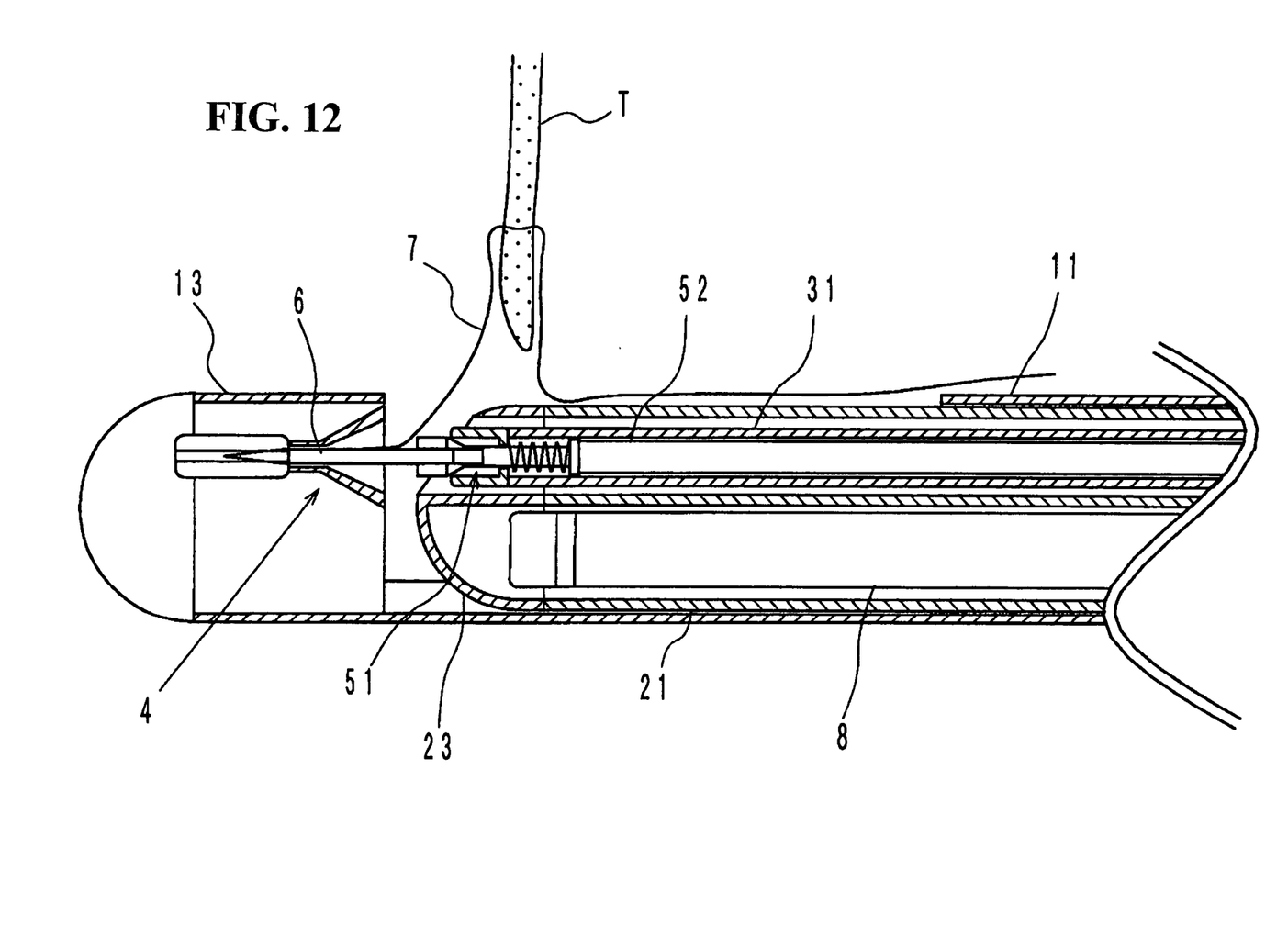
FIG. 12 is a schematic diagram illustrating suture operation using the intracardiac suture device of the present invention.

Next, the second shaft assembly 2 is pushed forward so that it take the position approximately the same position illustrated in FIG. 7. Then, the handling portion 54 of the puncture assembly 5 is moved to a position closed to the handling portion 33 while holding the operating portions 33 and 54, so that the enlarged head portion 552 of the second needle-holding means 51 is unsheathed from the third shaft 31 and the hollow member 55 is released from the compression pressure of the third shaft 31. Thus, the hollow member 55 is returned to the uncompressed condition where the inner diameter of the hollow member 55 is larger than the outer diameter of the suture needle 6. At that time, the coil spring 53 is being compressed. Under such conditions, the third shaft assembly 3 is advanced in connection with the second shaft assembly 2 by pushing the handling portion 33, so that the suture needle 6 is received by the second suture needle-holding means 51 as illustrated in FIG. 12.

Figure 13:
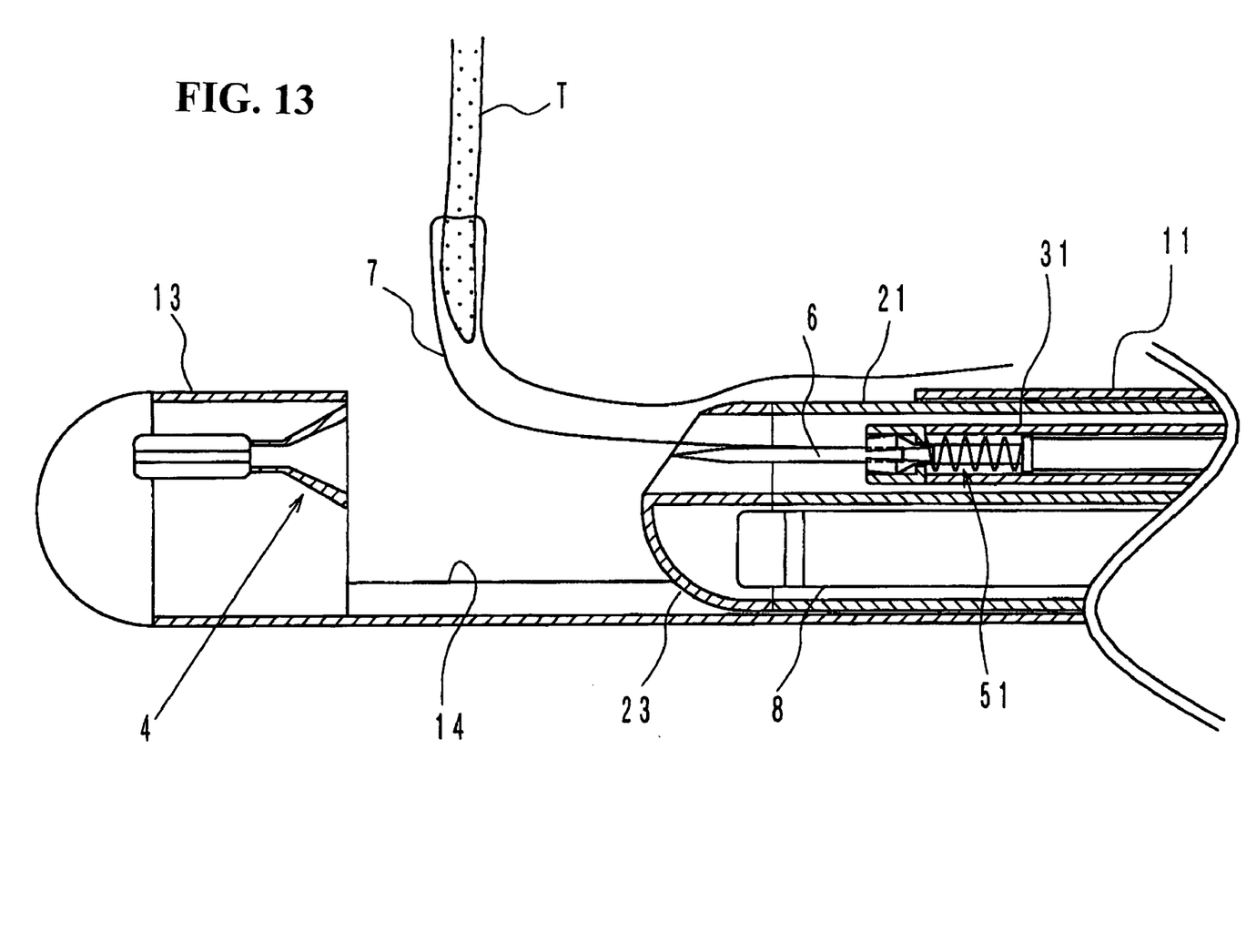
FIG. 13 is a schematic diagram illustrating suture operation using the intracardiac suture device of the present invention.

Then, by taking off the handling portion 33 while holding the second shaft assembly 2 and the handling portion 54 of the puncture assembly 5, the third shaft assembly 3 is moved forward by the restoring force of the coil spring 53. For this reason, the enlarged head portion 552 is received in the third shaft 31 and the hollow member 55 is compressed by the third shaft 31 to make the inner diameter of the hollow member 55 smaller than the outer diameter of the suture needle 6. And thus, the suture needle 6 is held by the suture needle-holding means 51. Under such conditions, the first shaft assembly 1 is pushed forward manually in connection with the second shaft assembly 2, the suture needle 6 is transferred to the second suture needle-holding means 51 and brought to the condition as illustrated in FIG. 13.

The closure of defect is completed by repeating the above procedures several times, and carrying out ligature and cutting of the suture with a special purpose device.

As will be understood from the above description, the use of the intracardiac suture device of the present invention makes it possible to perform a minimally invasive operation for suturing intracardiac defects without use of any artificial heart-lung system.

Further, the present invention makes it possible to perform intracardiac operations certainly and safely at a lower cost as compared with the conventional operations using any artificial heart-lung system. In addition, the present invention makes it possible to minimize risk of complications after the operation since the recovery time after operation is reduced to about one day, which is very short as compared with the recovery time of more than one week. Also, the present device is easy to operate and contribute to reduce burdens for an operator.

What is claimed is:

1. Art intracardiac suture device, comprising:
    a first shaft assembly comprising a first shaft having a lumen passing therethrough from a proximal end to a distal end thereof, a first suture needle-holding means coaxially provided at and spaced from the distal end of the first shaft, and a first connector provided on the proximal end of the first shaft;
    a second shaft assembly comprising a second shaft slidably arranged in the first shaft assembly, and a second connector provided on the proximal end of the second shaft, said second shaft having first and second lumens passing therethrough from a proximal end thereof to a distal end thereof, said second lumen being closed at a distal end thereof with a transparent covering member;
    a third shaft assembly comprising a hollow third shaft slidably arranged in the first lumen of said second shaft assembly, and a handling portion provided at a proximal end of the third shaft; and
    a puncture assembly comprising a hollow operating rod provided at a distal end thereof with a second suture needle-holding means movably arranged in the distal end of the third shaft, said hollow operating rod being connected to the proximal end of the second suture needle-holding means and movably arranged in the third shaft assembly;
    and a visual monitoring means arranged in the distal end of the second lumen at a position close to the distal end of said cover member;
    wherein said second shaft is protrusible by sliding-movement from the distal end of the first shaft toward the first suture needle-holding means, and wherein a suture needle is transferable between the first suture needle-holding means and the second suture needle-holding means when the third shaft is slid to the distal end of the second shaft after sliding the second shaft to a position where a suture site is held between said covering member and the first suture needle-holding means.

2. The intracardiac suture device according to claim 1, wherein the second shaft assembly is rotatable in the first shaft assembly.

3. The intracardiac suture device according to claim 2, wherein said visual monitoring means is an endoscope or ultrasonic transducer.

4. The intracardiac suture device according to claim 1, wherein said visual monitoring means is an endoscope or ultrasonic transducer.

5. The intracardiac suture device according to claim 1, wherein the second connector is provided with a pair at rotationally symmetrical protrusion extending front the peripheral portion toward the distal end thereof, and wherein said first connector is provided on its proximal end side with a pair of recesses for receiving said protrusions, and wherein said second shaft is movable between a position where the protrusions are respectively received in said recesses and a position where the protrusions are disengaged from said recesses.

6. The intracardiac suture device according to claim 1, wherein either or both connectors of the first and second shaft assemblies are provided with a side tube for infusion of heparin, a saline solution or the like.

* * * * *